United States Patent [19]

Manhart

[11] 4,375,968

[45] Mar. 8, 1983

[54] THERAPEUTIC CALCIUM HYDROXIDE DENTAL PREPARATION AND METHOD

[76] Inventor: Mark J. Manhart, 727 Medical Arts Bldg., Omaha, Nebr. 68102

[21] Appl. No.: 281,978

[22] Filed: Jul. 10, 1981

[51] Int. Cl.³ .............................................. A61K 6/08
[52] U.S. Cl. ...................................... 433/217; 106/3; 106/35; 424/49; 424/145; 433/168
[58] Field of Search .......................... 106/35; 433/217

[56] References Cited

U.S. PATENT DOCUMENTS 3,047,408  7/1962  Dougherty ............................ 106/35
4,240,832  12/1980  Jandourek .............................. 106/35

*Primary Examiner*—Lorenzo B. Hayes
*Attorney, Agent, or Firm*—Zarley, McKee, Thomte, Voorhees & Sease

[57] ABSTRACT

This invention relates to a dental material containing calcium hydroxide in a controlled condition.

The material is formulated in a particular way allowing it to be used successfully in a variety of therapies. The various mixtures and methods of using the calcium hydroxide materials are herein disclosed. In addition, mixtures of the calcium hydroxide material for specific therapies are also disclosed.

3 Claims, No Drawings

THERAPEUTIC CALCIUM HYDROXIDE DENTAL PREPARATION AND METHOD

BACKGROUND OF THE INVENTION

1. Field of the Invention

This invention relates to a calcium hydroxide composition and methods for its use on both hard and soft dental tissues.

2. Prior Art

Caustic mixtures of calcium hydroxide have been used in dentistry since the 19th Century as a temporary filling material within the tooth, or as a dental cavity lining material. Concentrated solutions of calcium hydroxide have been used in medicine for treatment of superficial skin wounds and burns of cutaneous skin tissues. More recently, several forms of calcium hydroxide have been used for specific pathological complications inside the tooth in the field of Endodontia.

A review of endodontic use of calcium hydroxide is provided in an article by Martin & Crabb appearing in the British Dental Journal of May 1977 entitled *Calcium Hydroxide in Root Canal Therapy*.

Generally, recent uses of calcium hydroxide preparations, including pastes, have been limited to dental pulp and root canal therapy. For example, one type of dental cavity lining material that has been particularly successful is disclosed in U.S. Pat. No. 3,047,408 to Dougherty. That patent discloses a dental composition used primarily as a dental cement. The Dougherty dental composition consists essentially of calcium hydroxide in a polyhydric phenol, combined with an ester of salicylic acid to form a calcium phenolate in which an excess of calcium hydroxide is dispersed.

The use of acid resistant, fast curing calcium hydroxide formulations for dental pulp capping and cavity lining has been more recently introduced. U.S. Pat. No. 4,240,832 to Jandourek discloses such a material. The dental material disclosed in U.S. Pat. No. 4,240,832 is prepared by reacting phenolic derivatives with formaldehyde.

Another example of endodontic therapy involving calcium hydroxide is described in the Omaha District Dental Society Journal, page 226 (Manhart). The article describes a method of endodontic sealing which uses a calcium hydroxide paste specifically designed for root canal closure (obliteration).

In addition, studies by Green, Green and McPhall in the Journal of Peridontology, 1977, Oct. 48(10), p. 887-72 on the treatment of hypersensitive root surfaces reinforce the potential value of calcium hydroxide preparation in endodontic therapy. Likewise, a method of using calcium oxide and water to form calcium hydroxide as a permanent endodontic filler is described by Donnelly and Harty in the Journal of the British Endodontic Society (1979).

Therefore, it is evident that calcium hydroxide has been extensively studied as a potentially valuable agent in controlling endodontic problems. However, the prior art teaches away from using calcium hydroxide in periodontal therapy. An example of such art can be found in the Dental Clinics of North America Journal of October, 1979, Vol. 23 p. 691-703 (Frank) on calcium hydroxide uses in dentistry. As shown in the Frank Article, the conventional experience is that calcium hydroxide pastes are too strong for the soft gingival or periodontal tissues. Accordingly, there is a need for a calcium hydroxide material which is formulated to control its strong alkaline properties so that it can be safely used on soft gingival and periodontal tissues.

Along with the need for the dental material, there is a corresponding need for methods for using the calcium hydroxide paste for treating soft tissue, bacterial infections and a variety of other dental complications. Nowhere in the dental literature or reference patents is there disclosed a comprehensive method of periodontal therapy using a controlled form of calcium hydroxide paste. The instant invention is directed toward these needs.

DETAILED DESCRIPTION OF THE INVENTION

Composition "A," comprised of calcium hydroxide, ethyltoluene sulfonamide, zinc stearate, and zinc oxide, forms the alkaline carrier of a two paste system. The ethyltoluene sulfonamide is a plasticizer. The zinc stearate is an emulsifier. The calcium hydroxide contains the prehydroxyl ions which create an alkaline environment that promotes healing of bacterial infections and desensitizing of tooth structure. The zinc oxide is a filler which moderates the reaction and makes the combination into a paste. The range of formulation in composition "A" is between fifty to fifty-four percent calcium hydroxide; thirty to thirty-seven percent ethyltoluene sulfonamide; nine to ten percent zinc oxide and 0.3 percent zinc stearate.

As previously mentioned, the carrier medium in the composition is the crucial material. It carries the calcium hydroxide in a medium which can be brought to the infectious tissue and allowed to react with the second composition to give off a stoichiometric excess of hydroxyl ions. A second composition, composition "B" contains a methyl salicylate liquid and a glycol. The methyl salicylate reacts with the glycol in a transesterification reaction to form new esters. These esters react with composition "A" to form a homogeous mass which slowly emits hydroxyl ions producing a mild alkaline effect in the tissue area. Composition "B" is essentially comprised of methyl salicylate (a salicylic acid ester) at approximately twenty to twenty-five percent, aqueous 1, 3 butylene glycol at twenty to twenty-five percent, and a titanium dioxide-calcium sulfate filler at fifty to seventy-five percent. The titanium dioxide-calcium sulfate filler acts as a reaction moderator to slow setting time.

Silica or flour of pumice filler could also be used to control the reaction speed instead of the titanium dioxide-calcium sulfate mixture.

When the two compositions ("A"&"B") are combined, the resultant paste sets quickly, so the zinc oxide moderator, of composition "A" is introduced to slow setting time of the final paste.

The ideal combination of the two pastes is one part of composition "A" mixed with two parts of composition "B". Nevertheless, it should be noted that the ratio of the two pastes may be varied considerably by the user without departing from the scope of this invention. The ideal combination of the two pastes sets in approximately four (4) minutes.

In the ideal concentration, the resultant paste composition mixes about three times as much calcium hydroxide as would normally react with the salicylic ester. That is, the rigid mass that results from this mixture contains three times as many hydroxyl ions as would normally react with the salicylic ester; thereby bringing an excess amount of hydroxyl ions into the environment. Even so, the calcium hydroxide is under control, as the excess hydroxyl ions are expended gradually to the bacterial environment, which generally exhibits an acidic condition. Accordingly, this process neutralizes the affected area. The soft tissue, bone tissue or tooth structure can then respond to the resulting neutral environment and reestablish a natural barrier to bacterial invasion or strong stimuli. Since this physiological mechanism proceeds in a buffered media, the soft tissues are not cauterized or damaged. The physiological mechanism of raising the pH in the area of infected tissue to a neutral level allows the tissue to regenerate.

More concentrated solutions of the calcium hydroxide can be used to desensitize cervical areas of teeth. The excess calcium hydroxide sets up an alkaline barrier on the tooth surface in as short a time as five minutes. The barrier will remain for as long as three months, thereby maintaining a neutral pH level. As a result, the tooth structure can establish its own natural barrier, within the cementum, to temperature and pressure changes.

A third composition can also be formulated for use on hypersensitive teeth or in endodontic medication of teeth. This composition is produced by combining two parts calcium oxide and one part zinc oxide, then mixing with four parts of ethylene glycol and one part water. This composition "C" material may be used in conjunction with the composition "A" and compostion "B" as a desensitizing agent for teeth by applying a film of the desensitizing material "C" around the hypersensitive cervex area of the tooth (dentino-enamel junction or root surface), and then covering the film with the two paste system "A" and "B". The hard mass system holds the material "C" in place to concentrate the effect of the alkaline solution in the sensitive area of the tooth.

An alternate method would be to apply an aqueous dispersion or organic solvent with calcium hydroxide in a film to the sensitive area of the tooth, and then cover that area with the more rigid calcium hydroxide two paste system. The material would be left on the tooth for four to five minutes, or up to several days, thereby eliminating the hypersensitivity. The composition "C" can also be used as an endodontic medication which is manipulated into the root canals of a tooth, sealed off with temporary cement and allowed to sedate the infected or abscessed tooth during the medication period prior to endodontic obturation.

Generally the calcium hydroxide pastes, and the methods for their use, provide a physiological balance in which the soft tissue can respond by setting up a very insoluble barrier that is slightly alkaline. When the barrier is maintained over a significant time, depending on the type and initial condition of the tissue, the tissues will respond favorably. As hydroxyl ions are gradually expended from the solidified mass or film layer on a tooth, the neutralizing effect stabilizes and reduces the tissue degeneration from bacterial invasion.

In addition, numerous practical applications of the calcium hydroxide paste system may be formulated. For example, a dental polishing agent can be prepared by combining composition "C" and pumice. This mixture stimulates soft gingival tissues, and promotes healing of irritated gingiva. Likewise, a therapeutic toothpaste can be formulated by combining material "A" and a modified version of material "B" to form a single paste. In this situation, material "B" would be modified to include approximately 19.6 percent methyl salicylate, 78.4 percent 1, 3 butylene glycol, and two percent gum. The final composition would be comprised of forty-nine percent material "A", and fifty-one percent material "B". Specific advantages of this paste include its desensitizing and antiseptic effects on teeth and gingiva.

Post extraction surgical dressings can also be formulated. These dressings are prepared in two different ways. First, a combination of material "C" and balsam of Peru, would create a desensitizing, antiseptic dressing. Second, a mixture of "A" and "B" (in a one to two ratio) to form a single paste could be combined with balsam of Peru to create a useful surgical dressing.

The calcium hydroxide two paste system also could be used to formulate various cements and sealants. For example, a radiographically visible root canal sealant can be made using a mixture of "A" and "B" in a one to two ratio (approximate). However, in this situation, material "B" further includes ten to fifteen percent barium sulfate.

The two paste system could also be used as a crown and bridge cement. The amount of zinc oxide in this preparation may be varied to control the setting time of the cement. Due to the alkaline properties of the material, solubility of the cement would remain low.

Accordingly, various combinations of the pastes may be used as essential components in other useful products. For example, specially treated dental floss could be made by impregnating untreated floss material with substance "C". Specially treated suture material could be made in the same way. A therapeutic, antiseptic mouthwash could be formulated using a mixture of seventy to seventy-five percent water, 1/10 percent flavor and twenty-five to thirty percent material "C". Temporary denture liners designed to tone tissue into a healthy condition could be made using a combination of eighty percent edentulous tissue conditioner, a product well known in the art, and twenty percent material "C". An example of such a tissue conditioner is made by Caulk Co. under the trademark "Tissue-Comfort". Another example is "Coe-Comfort" manufactured by Coe Laboratories, Inc. Another method of making an effective temporary immediate denture liner involves a combination of "A" and "B" in a three to one ratio. The resulting combination paste could then be used alone or in combination with tissue conditioner in a one to ten ratio.

Other additional uses for the calcium hydroxide system include a therapeutic gingival paste consisting of a two to one mixture of "B" and "A" respectively. However, "A", in this situation, is modified to include 58.4% calcium hydroxide, 41.3% ethyltoluene sulfonamide, and 3/10 percent zinc stearate.

A dental sedative cream can be formulated using a three to one (approximate) combination of "A" and "B" to form a single paste.

A periodontal staining paste can be formed by combining paste "A" and "B" in a one to two ratio (approximate). However, in this situation, a variable amount of a bacterial staining agent well known to the art would be added to "B" initially.

Finally, two therapeutic, antiseptic prophylactic pastes could be produced using mixtures of material "A" and "B". The first paste would contain a mixture of "A" and "B" in a one to two ratio (approximate). Material "B" in this case would be modified by replacing the fifty to seventy-five percent titanium dioxide-calcium sulfate filler with fifty to seventy-five percent silica or flour of pumice. The second paste would be made in the same way as the first paste, with one exception. In the second paste, material "B" would contain twenty-five to thirty-five percent methyl salicylate, and fifty to seventy-five percent silica or flour of pumice (the 1, 3 butylene glycol is eliminated). The second type of paste would create conditions of greater alkalinity, due to the increased amount of methyl salicylate which is available to form esters which react with the calcium hydroxide when the two pastes are combined.

The material of this invention may be used in a therapeutic method of treating tissues comprising the following steps:
 (a) drying the area to be treated;
 (b) applying the material to the area to be treated; and
 (c) allowing the material to harden.

The preferred material in the method described hereinabove is comprised of calcium hydroxide, ethyltoluene sulfonamide, zinc stearate, methyl salicylate, 1,3 butylene glycol and titanium oxide-calcium sulfate filler in the proportions previously described. If desired, the material, while hardening, may be covered with a non-engenol periodontal surgical pack. It is recommended that the material be allowed to remain in place from one day to seven days before removing or replacing the same.

Although specific components, proportions, and process steps have been stated in the above description of the preferred embodiments of the invention, other suitable materials, proportions and process steps may be used with satisfactory results in varying degrees of quality. In addition, it will be understood that various other changes of the details, materials, steps and uses which have been herein described in order to explain the nature of the invention will occur to and may be made by those skilled in the art, upon a reading of this disclosure and such changes are intended to be included within the principles and scope of this invention as claimed.

I claim:

1. A therapeutic method of treating gingival and periodontal tissues of the mouth comprising the steps of:
 (a) drying the area to be treated;
 (b) providing a material comprised of calcium hydroxide, ethyltoluene sulfonamide, zonc stearate, methyl salcylate, 1,3 butylene glycol and titanium oxide-calcium sulfate filler;
 (c) applying the material to the area to be treated; and
 (d) allowing the material to harden.

2. The therapeutic method of treating gingival and periodontal tissues of the mouth, as described in claim 1, further comprising the additional step of covering the material with a non-engenol periodontal surgical pack.

3. The therapeutic method of treating gingival and periodontal tissues of the mouth, as described in claim 2, further comprising the additional step of allowing the material to remain in place from 1 day to 7 days before removing or replacing the material.

* * * * *